United States Patent [19]

Pandey et al.

[11] Patent Number: 5,864,035
[45] Date of Patent: *Jan. 26, 1999

[54] SYNTHESIS OF ISOIMIDE OF CHLORINS AND BACTERIOCHLORINS AND THEIR USE FOR DIAGNOSIS AND TREATMENT OF CANCER

[75] Inventors: Ravindra K. Pandey, Williamsville; Andrei N. Kozyrev, Amherst; Thomas J. Dougherty, Grand Island, all of N.Y.

[73] Assignee: Health Research, Inc., Buffalo, N.Y.

[ * ] Notice: The term of this patent shall not extend beyond the expiration date of Pat. No. 5,770,730.

[21] Appl. No.: 812,029

[22] Filed: Mar. 6, 1997

Related U.S. Application Data

[63] Continuation-in-part of Ser. No. 613,134, Mar. 8, 1996.
[51] Int. Cl.$^6$ .................................................. C07D 487/22
[52] U.S. Cl. ............................................ 540/472; 540/460
[58] Field of Search ............................................... 540/472

[56] References Cited

U.S. PATENT DOCUMENTS

| | | | |
|---|---|---|---|
| 5,459,159 | 10/1995 | Pandey et al. | 514/410 |
| 5,591,847 | 1/1997 | Pandey et al. | 540/472 |

OTHER PUBLICATIONS

Lee et al., J. Chem. Soc. Perkin Trans. 1. 1993, 2369–77.
Fieser and Fieser, Reagents for Org. Syn, vol. 1, 1967, pp. 233, John Wiley and Sons, Inc., New York.
Sripada et al., J. Lipid. Res., vol. 28, 1987, pp. 710–718.
Chang, C. et al., *Differentiation of Bacteriochlorin and Isobacteriochlorin Formation by Metallation. High Yield Synthesis of Porphyrindiones via OsO$_4$Oxidation*,J. Chem. Soc., Chem. Commun., pp. 1213–1215 (1986).
Beems, E. et al., *Photosensitizing Properties of Bacteriochlorophyllin a and Bacteriochlorin a, Two Derivatives of Bacterchlorophyll a*, Photochemistry and Photobiology, vol. 46, No. 5 pp. 639–643 (1987).
Dougherty, T. et al., *Photoradiation Therapy. II. Cure of Animal Tumors With Hematoporphyrin and Light,* Journal of the National Cancer Institute, vol. 55, No. 1, pp. 115–119 (1975).
Evensen, J. et al., *Photodynamic Therapy of C3H Mouse Mammary Carcinoma with Haematoporphyrin di–ethers as Sensitizers,*Br. J. Cancer, 55, pp. 483–486 (1987).
Diamond, I. et al., *Photodynamic Therapy of Malignant Tumors,*The Lancet, pp. 1175–1177 (1972).
Lipson, R. et al. *The Use of a Derivative of Hematoporphyrin in Tumor Detection,*Journal of the National Cancer Institute, vol. 26, No. 1, pp. 1–10 (1961).
Pandey R. et al., *Substituent Effects in Tetrapyrrole Subunit Reactivity and Pinacol–Penacolone Rearrangements: VIC–Dihydroxychlorins and VIC–Dihydroxybacteriochlorins,*Tetrahedron Letters, vol. 33, No. 51, pp. 7815–7818 (1992).

Hoober, K. et al., *Photodynamic Sensitizers from Chlorophyll: Purpurin–18 and Chlorin p$_6$*, Photochemistry and Photobiology, vol. 48, No. 5, pp. 579–582 (1988).
Pandey R. et al., *Structure/Activity Relationships Among Photosensitizers Related to Pheophorbides and Bacteriopheophorbides,*Bioorganic & Medical Chemistry Letters, vol. 2, No. 5, pp. 491–496 (1992).
Pandey R. et al., *Chemistry of Photofrin II and Some New Photosensitizers,*SPIE vol. 1065 Photodynamic Therapy: Mechanisms, pp. 164–174 (1989).
Pandey et al., *Fast Atom Bombardment Mass Spectral Analyses of Photofrin II®and its Synthetic Analogs,*Biomedical and Environmental Mass Spectrometry, vol. 19, pp. 405–414 (1990).

*Primary Examiner*—Mukund J. Shah
*Assistant Examiner*—Pavanaram K. Sripada
*Attorney, Agent, or Firm*—Michael L. Dunn

[57] ABSTRACT

Compounds having utility as light absorbing compounds, especially in the area of photodynamic therapy. Such compounds have the formula:

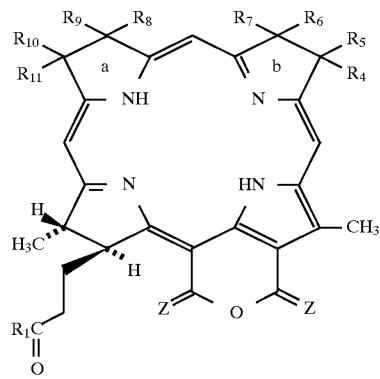

where z is =O or $NR_{14}$; $R_{14}$ is alkyl or substituted alkyl; $R_1$ is an amino acid group, a polyamine group, a polyether group or $OR_{13}$ where $R_{13}$ is alkyl; $R_4$ through $R_{11}$ are —H, —OH alkyl, alkoxy, alkenyl, alkylene, aryl, or aryloxy, or a carbonyl containing group, wherein carbon containing groups may be substituted with carbonyl, hydroxy, phosphoro, carboxy, halo, sulfo, amino and ether substituents, provided that; $R_4$ may be taken together with $R_7$ to form =O; $R_8$ may be taken together with $R_9$ to form =O; $R_{10}$ may be taken together with $R_{11}$ to form =O; and $R_4$ and $R_7$ may together form a chemical bond and $R_8$ and $R_{11}$ may together form a chemical bond; and $R_{12}$ is hydrogen or lower alkyl; provided that if one z is O, the other z is —$NR_{14}$.

16 Claims, 7 Drawing Sheets

FORMATION OF ANHYDRIDE RING ized, only in higher concentrations than in normal## SYNTHESIS OF ISOIMIDE OF CHLORINS AND BACTERIOCHLORINS AND THEIR USE FOR DIAGNOSIS AND TREATMENT OF CANCER

BACKGROUND OF THE INVENTION

This is a continuation-in-part of U.S. patent application Ser. No. 08/613,134, filed Mar. 8, 1996.

This invention relates to treatment and diagnosis of cancer through the use of IR imaging and photodynamic therapy employing porphyrin related compounds and more particularly certain analogs of chlorins and bacteriochlorins.

Photosensitizers are chemicals which kill cells and/or fluoresce when activated by light of a specific wavelength. Most malignant and some premalignant tissues retain these photochemically active substances in higher concentrations and for longer durations than surrounding normal tissues. The retention time is not dependent on whether or not the cells are synthesizing DNA or undergoing cell growth or nutrient uptake.

Light sensitive drugs, lasers and fiber optic probes have been combined in a procedure known as photodynamic therapy (PDT). PDT has emerged as one of the most promising strategies in cancer treatment (including cancer detection). PDT is being increasingly used where chemotherapy, surgery and high energy irradiation have failed. In this new therapy, patients are given intravenous injections of a photodynamic drug that accumulates in cancer cells in much higher concentrations than in normal cells. The photodynamic (photosensitizing) drug is then activated to kill the cancer cells by a laser beam directed to cancer cells through fiber optics. People who are too old or too frail to tolerate the stress of major surgery, chemotherapy or high energy radiation may be helped by photodynamic therapy, which often requires just local anesthesia and does not necessitate hospital admission. PDT is an important form of cancer therapy that has many additional advantages, e.g. it can be performed any number of times on a single patient, it is not contraindicated with other cancer therapies and it allows selective treatment of malignant tissues due to preferential retention of dye in cancer cells and it has already been established that for early or superficial malignancy, PDT may be curative.

Photosensitizers have been recognized for almost a century. In 1900, (Rabb, C., Z. Biol., 1900, 39, 1423) reported the lethal effects of a combination of acridin orange dye and ordinary light on Paramecium. In 1903, von Tappeneir reported the first therapeutic use of photosensitizers when he used eosin and white light to treat skin tumors. The phototoxic effect of an administered porphyrin in man was observed in 1913. The localization of administered porphyrins in tumor tissue was recognized in the 1940's. It was not until 1972, however, that these two ideas (photodegradation of tissue and localization in tumors) came together successfully, when Diamond demonstrated that a porphyrin could preferentially degrade tumor implants in a rat (Diamond, I.; McDonagh, A. F.; Wilson, C. B.; Granelli, S. G.; Nielsen, S.; Jaenicke, R., Lancet, 1972, 1175). This result was confirmed and extended by Dougherty, T. J.; Grindey, G. B.; Fiel, R.; Weishaupt, K. R.; Boyle, D. G.; *J. Natl. Cancer Inst.*, 1975, 55, 115.

The higher concentration of porphyrins in malignant tumors is used for the treatment and detection of cancer. For detection of early stage small tumors, the porphyrin-containing tumor cells and surrounding tissues are exposed to light. The porphyrins then emit a strong fluorescence, which contrasts with the much weaker fluorescence from the normal tissue, allowing for detection. For the treatment of cancer, photodynamic therapy (PDT) consists of injecting the patient with a photoactive dye and irradiating the tumor area with a wavelength of light which activates the dye to produce toxins which kill the tumor. The porphyrin dyes become toxic to the surrounding environment by producing single oxygen and oxygen radicals (Dougherty, T. J.; Kaufman, J. H.; Goldfarb, A.; Weishaupt, K. R.; Boyle, D.; Mittleman, A.; *Cancer Res.*, 1976, 38, 3628). PDT techniques depend strongly on how well the compound used preferentially concentrates within the tumor cell. Skin photosensitivity is the only known side effect of PDT with certain porphyrin type photosensitizers. Because skin retains these chemicals in enough quantities to produce surface reactions, patients must avoid exposure to sunlight.

The distribution of porphyrin drugs in the body compared with tumor cells is still under investigation. The distribution varies with cell type and porphyrin derivative. It is thought that once the photosensitizer is injected intravenously, some of the drug escapes the blood stream and moves into the interstitial fluid. The porphyrin binds to the cellular membrane and slowly diffuses into the cell cytoplasm. Each porphyrin, then, rapidly binds to hydrophobic regions inside the cell. Fluorescence microscopy of porphyrin-treated leukemia L1210 cells shows a localization around the plasma membrane and within the intracellular vesicles.

Photofrin®, a hematoporphyrin derivative (Dougherty, T. J.; Boyle, D. G.; Weishaupt, K. R., "Photodynamic Therapy—Clinical and Drug Advances, Porphyrin Photosensitization," *Plenum Press*, New York, 1983, p. 3) is the only photosensitizer currently being used all over the world for the treatment of a variety of solid tumors. Hematoporphyrin derivative (Hpd) is prepared by mixing hematoporphyrin with glacial acetic acid and sulfuric acid, followed by hydrolysis and precipitation under acidic conditions. This method was partially described by Lipson et al. (Lipson, R. L.; Baldes, E. J.; Olsen, A. M., *J. Natl. Cancer Inst.*, 1961, 26, 1). Hpd thus produced consists of a variety of porphyrins. When Hpd is separated into its two main fractions by gel filtration with Sephadex LH-20, the higher molecular weight portion, called Photofrin®, is a more efficient PDT agent (Dougherty, T. J.; Boyle, D. G.; Weishaupt, K. R.; Henderson, B.; Potter, W.; Bellnier, D. A.; Wityk, K. E., *Adv. Exp. Biol. Med.*, 1983, 160, 3). The recommended human dosage of Photofrin® is 1–2 mg/kg of body weight. The main components of Photofrin® are dimers and higher oligomers linked with ether, and possibly carbon-carbon linkages (Pandey, R. K.; Siegel, M. M.; Tsao, R.; McReynolds, J. M.; Dougherty, T. J., *Biomed. and Environ. Mass Spectrometry*, 1990, 19, 405).

For a photosensitizer to be clinically useful, it must be non-toxic, selectively taken up and/or retained in malignant tissues, activated by penetrating light (>600 nm), and photochemically efficient. Although Photofrin® has been approved for commercialization in Canada, Europe and the United States, it lacks rapid clearance from tissues, is a complex mixture of oligomers, and has the disadvantage that its absorbance at 630 nm is not optimized for tissue penetration. New porphyrin photosensitizers are thus needed for the improvement of photodynamic therapy for cancer treatment.

There is a need for more efficient, chemically pure, less phototoxic, and better localizing porphyrins. Important prior art porphyrin and chlorin derivatives have been reviewed by Pandey, R. K.; Majchrzycki, D. F.; Smith, K. M.; Dougherty, T. J., *Proc. SPIE*, 1989, 1065, 104. The aspartyl derivatives of chlorin $e_6$, monoaspartyl chlorin $e_6$ and diaspartyl chlorin $e_6$, were found to be effective photosensitizers in vitro (Roberts, W. G.; Shaiu, F. Y.; Nelson, J. S.; Smith, K. M., Roberts, M. W., *J. Natl. Cancer Inst.*, 1988, 80, 330). With these compounds, the aspartyl group was noted to be responsible for the efficiency of tissue clearance. In pheophorbide, pyropheophorbide and chlorin $e_6$ series, certain alkyl ether derivatives including 2-(1-hexyloxyethyl)2-des vinyl derivatives were found to be excellent photosensitizers compared with parent compounds, methyl pheophorbide-a, pyropheophorbide- and chlorin$_6$. (Pandey, R. K.; Bellnier, D. A.; Smith, K. M.; Dougherty, T. J., *Photochem. Photobiol.*, 1991, 53, 65). This was attributed to the increased hydrophobicity of the hexyl group and is consistent with studies done by Evenson on porphyrins with varying polarities (Evenson, J. F.; Sommer, S.; Riminfton, C.; Moan, J., *Br. J. Cancer,* 1987, 55, 483).

Chang, C. K., Sotiroiu, C.; Wu, W., *J. Chem. Soc., Chem. Commun.,* 1986, 1213, have previously shown that chlorins, on reacting with osmium tetroxide can be converted to vic dihydroxy bacteriochlorin system. This methodology has been extended in the pheophorbide-a and chlorin $e_6$ series, by preparation at a series of vic -dihydroxy and keto-bacteriochlorins (Pandey, R. K.; Shiau, F. Y.; Sumlin, A. B.; Dougherty, T. J.; Smith, K. M., *Bioorg. & Med. Chem. Lett.,* 1992, 2, 491). It has also been reported that the regiospecificity of pyrrole subunits in osmium tetroxide oxidation is affected significantly by the presence of electron withdrawing substituents in the macrocycle (5a). These stable bacteriochlorins, prepared from mesochlorin $e_6$ trimethylester and pyropheophorbide-a methylester, have strong absorption in the red region (730 to 750 nm), but, did not show any significant in vivo photosensitizing activity (Kessel, D.; Smith, K. M.; Pandey, R. K.; Shaiu, F. Y.; Henderson, B., *Photochem. Photobiol.,* 1993, 58, 200).

Hoober, J. K.; Sery, T. W.; Yamamoto, Y., *Photochem. Photobiol.,* 1988, 48, 579 showed that purpurin-18 2, which has strong absorption at 700 nm might be a useful photosensitizer for photodynamic therapy (PDT).

Among long wavelength absorbing photosensitizers, bacteriochlorins have been proposed as potential useful candidates for use in photodynamic therapy (PDT) where strong absorptions in the visible spectrum can be used to photoactivate dyes previously located in targeted (neoplastic) tissues (Pandey, R. K.; Shiau, F. Y.; Isaac, M.; Ramaprasad, S.; Dougherty, T. J.; Smith, K. M., *Tetrahedron Lett.,* 1992, 33, 7815). Some naturally occurring bacteriochlorins, have previously been reported as effective photosensitizers both in vitro and as in vivo (Beems, E. M.; Dubbelman, T. M. A. R.; Lugtenburg, J.; Best, J. A. B.; Smeets, M. F. M. A.; Boehgeim, J. P. J., *Photochem. Photobiol.,* 1987, 46, 639). However, most of the naturally occurring bacteriochlorins (760–780 nm) are extremely sensitive to oxygen, which results in rapid oxidation to the chlorin state (640 nm); thus the spectroscopic properties of the bacteriochlorins are lost. Further, if a laser is used to excite the bacteriochlorin in vivo, oxidation may result in the formation of a new chromophore absorbing outside the laser window, thus reducing the photodynamic efficiency.

It has been found that certain cyclic amide derivatives of porphyrins, including bacteriochlorins and chlorins, have both an increased wavelength and the requisite stability to meet the requirements of an improved photodynamic therapeutic agent. Unfortunately, the preparation of such compounds is difficult and yields are very low, e.g. 10 to 30%. Such compounds (e.g. compound 8) have in the past been prepared by cyclizing chlorin-$P_6$ 6-N-hexylamide-7-methyl ester 3A (compound 3 reacted with diazomethane). The resulting cyclized reaction mixture contains a number of products in addition to the cyclic amine, especially unreacted starting material 3A. The synthesis route therefore is not only inefficient because of low yield, but requires significant subsequent purification. Further such compounds have not had optimal hydrophylic-lipophylic balance.

BRIEF DESCRIPTION OF THE INVENTION

Figure 1:
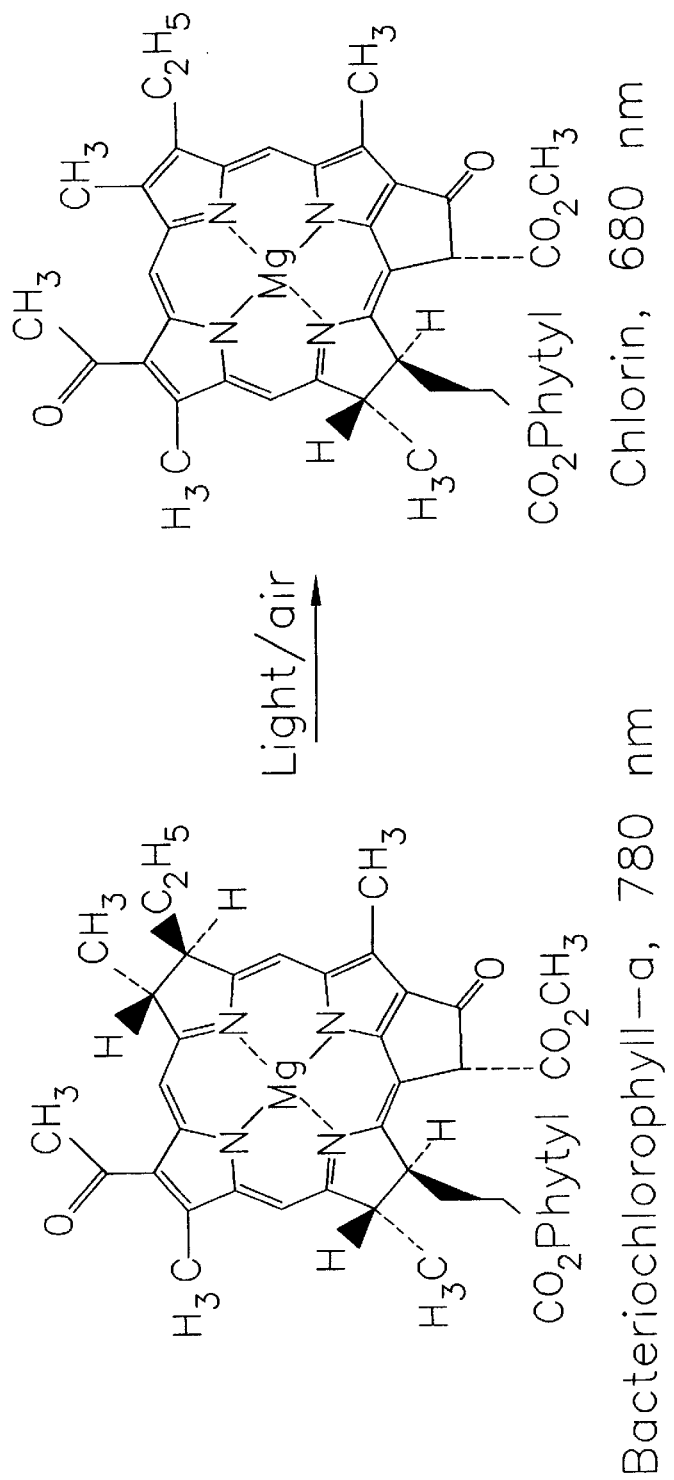
FIG. 1 is a schematic equation showing the degeneration of bacteriochlorophyll-a to chlorin.

In accordance with the present invention, there are provided new chlorin and bacteriochlorin derivatives having utility as fluorescent and photosensitizing compounds. Such compounds may be excited by microwaves, ultrasound, and visible or infrared radiation.

All of such novel compounds described herein may be used in traditional areas where compounds having such properties have utility. The compounds, may, for example, be incorporated into a substance such as a plastic product, excited with ultrasound, microwaves or visible light followed by using known methods for detecting emitted radiation to image the product for the purpose of detecting voids or other flaws in the product.

Certain of such compounds have special utility as photosensitizers in the area of photodynamic therapy for the detection and treatment of tumors.

In accordance with the invention, to make PDT more applicable, there is a need of long wavelength absorbing photosensitizers such as stable bacteriochlorins which have the ability to localize in high concentration at the tumor site.

Furthermore there is a need for an efficient and cost effective method for preparing such photosensitizers.

In accordance with the invention, a compound is therefore provided which comprises a chemical of the formula:

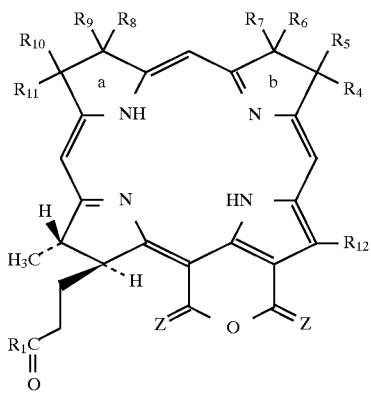

wherein z is =O or =NR$_{14}$; R$_1$ is an amino acid group, a polyamine group, a polyether group or OR$_{13}$ where R$_{13}$ is alkyl; R$_{14}$ is alkyl, or substituted alkyl, a polyamine group, or an amino acid group; R$_4$ through R$_{11}$ are —H, —OH, alkyl, alkylene, —OR$_{16}$, where R$_{16}$ is H, alkyl or aryl, or a carbonyl containing group, provided that; R$_4$ may be taken together with R$_5$ to form =O; R$_6$ may be taken together with R$_7$ to form =O; R$_8$ may be taken together with R$_9$ to form =O; R$_{10}$ may be taken together with R$_{11}$ to form =O; and R$_4$ and R$_7$ may together form a chemical bond and R$_8$ and R$_{11}$ may together form a chemical bond; and R$_{12}$ is hydrogen or lower alkyl; provided that if one z is =O, the other z is =NR$_{14}$.

The invention further includes a method for using the above compound as an intermediate for the preparation of additional long wave length stable photosensitizers and a method for its preparation.

DETAILED DESCRIPTION OF THE INVENTION

The invention permits more flexibility in the preparation of porphyrin-type compounds than was previously possible. Intermediate compounds may be provided with a number of substituents on the a and b rings and variable substituents at R$_1$.

The a and b rings may be saturated or unsaturated at the R$_4$–R$_{11}$ positions or may contain hydrogen, hydroxy, formal or substituted and unsubstituted alkyl, alkoxy, alkenyl, aryl, and aryloxy groups. The alkyl, alkoxy, alkenyl, aryl and aryloxy groups usually contain 1 through 8 carbon atoms and more commonly contain 1 through 3 carbon atoms. A limited number, i.e., as many as 2, of such carbon containing groups may be long chain carbon containing groups, e.g., up to 22 carbon atoms.

The carbon containing groups may be substituted with carbonyl, hydroxy, phosphoro, carboxy, halo, sulfo, amino and ether substituents.

Figure 2:
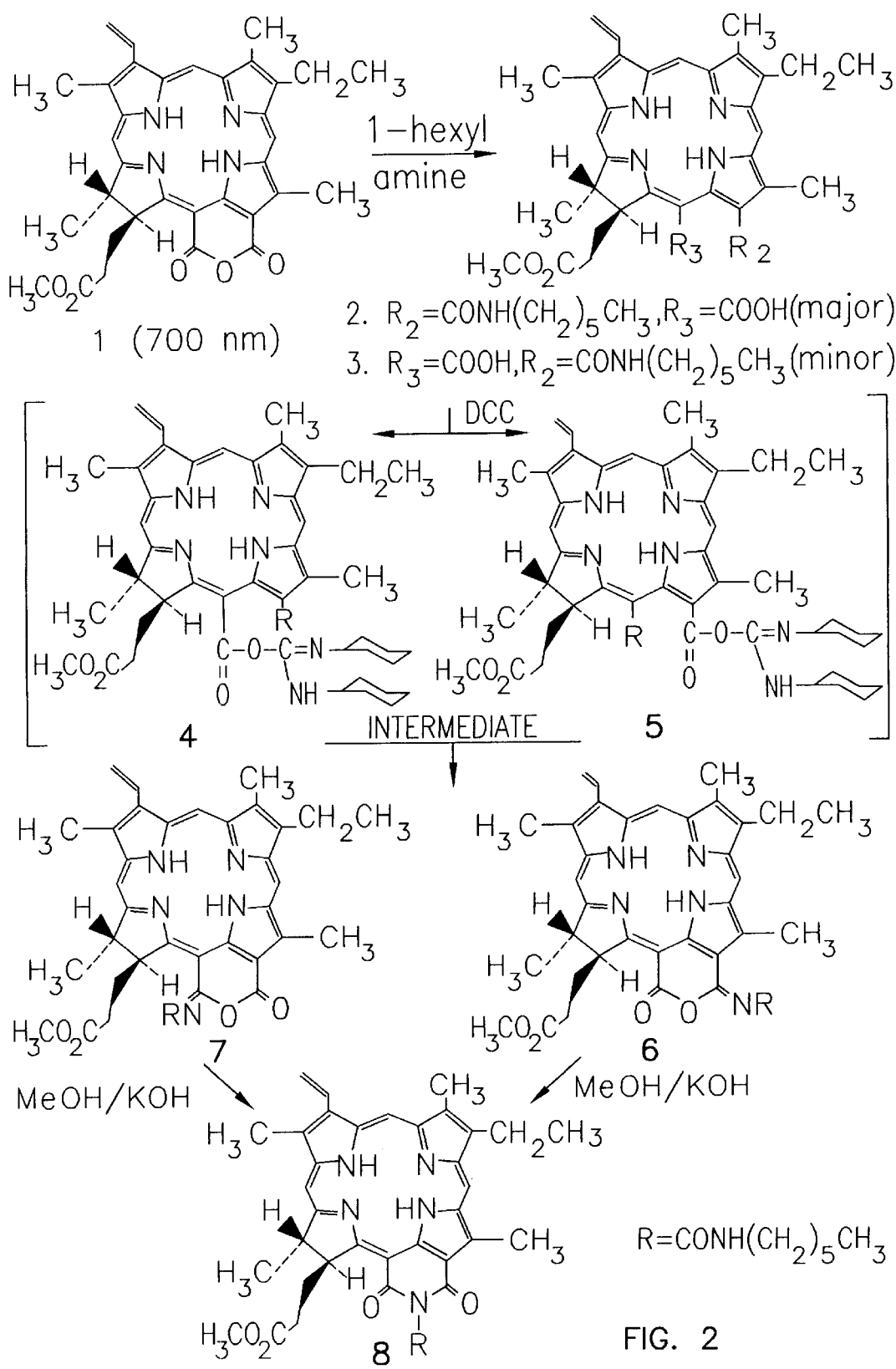
FIG. 2 is a schematic equation showing the synthetic route to compounds 6 and 7 of the invention and their use as intermediates to compound 8.
Figure 3:
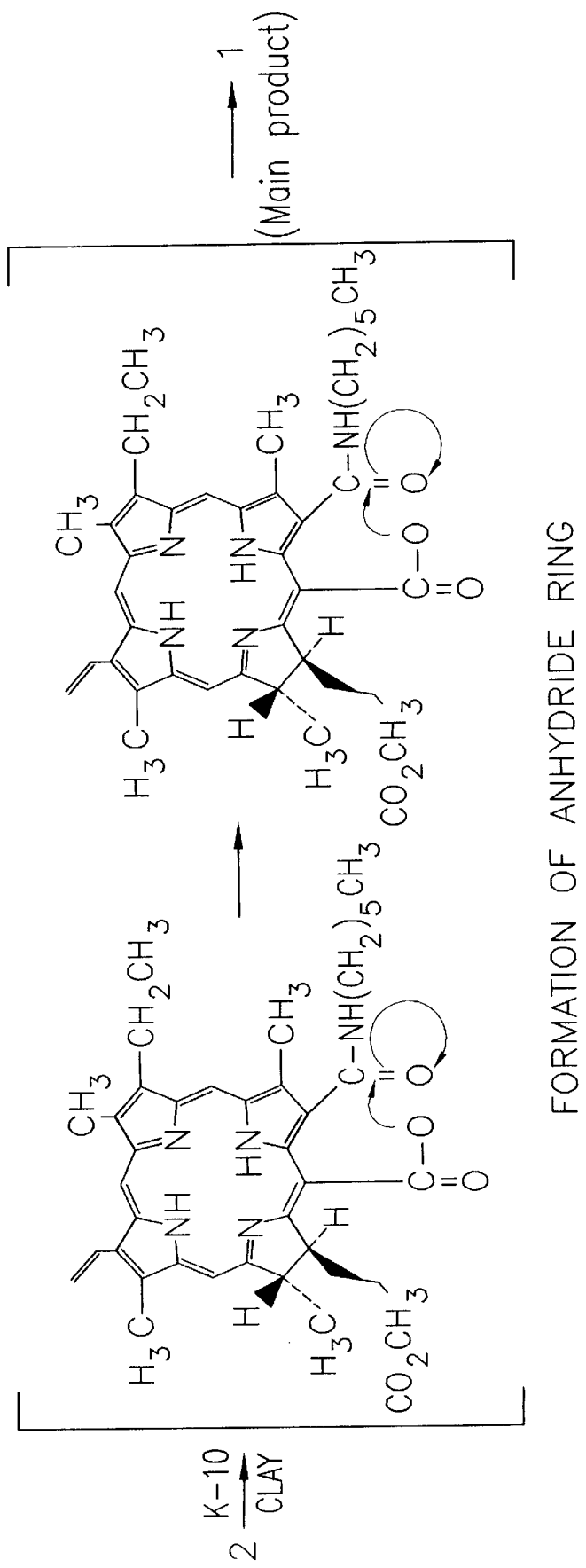
FIG. 3 is a schematic equation showing the synthetic route to cyclic anhydride, compound 1.

To obtain the compounds of the invention, a substituted or unsubstituted chlorin or bacteriochlorin is reacted by known methods, as described in Kenner et al., *J. Chem. Soc.*, Perkin Trans. I, 1973, 2517, to obtain a six membered anhydride ring fused to the macrocyle. For example, to obtain a suitable bacteriochlorin, bacteriochlorophyll a is converted to bacteriopurpurin-a containing an anhydride ring before subjecting it to the subsequent reactions described herein. The anhydride is then reacted with 1, hexyl amine to open the anhydride ring, e.g., as shown in FIG. 2 to obtain 6 carboxylhexyl amide 2 and γ-carboxy-hexylamide 3.

The 6 carboxyhexylamide and the γ-carboxyhexylamide are then reacted separately or together with a carbodiimide to form a porphyrin diimide which is unstable and immediately converts to an isoimid, the compound of the invention. A preferred carbodiimide is dicyloberylcarbodiimide (DCC), which results in compounds similar to 6 and 7 in FIG. 2 where the R$_1$–R$_{12}$ substituents may vary as described herein.

The invention may be described in more detail by reference to the following specific embodiment.

Initially, in order to establish the reaction conditions, purpurin-18 methyl ester 1 was used as the starting material. As expected, reaction of 1 (λmax 700 nm) with 1-hexylamine gave the corresponding amides in 95% yield as a mixture of 2 and 3 in the ratio of 9 to 1 (determined by using proton NMR) with λmax at 665 nm. Attempts to convert the amides 2 or 3 into the corresponding imides by following the methods used in converting aromatic anhydrides into imides, (e.g. such as heating with imidazole at 140° C.) mainly gave decomposition products. Leaving the amide solution in dichloromethane or tetrahydrofuran at room temperature for a week gave a mixture of purpurins with cyclic anhydride 1 (700 nm), cyclic imide 8 (705 nm) in minor amounts and the starting material as a major product. By refluxing the reaction mixture at various temperatures, slightly improved the yield of purpurin-anhydride without formation of any desired imide analogue. Various attempts were then made to optimize the reaction conditions, as summarized in Table 1. Reaction of amides 2 and 3 with K-10 clay using CH$_2$Cl$_2$ as a solvent again gave a mixture of cyclic imide 8 as minor product (12%) and anhydride analog 1 as major product (85%), which were easily separated by column chromatography. Reaction of purpurin amides (a mixture of 6-carboxyhexylamide 2 and γ-carboxy-hexylamide 3) with DCC afforded corresponding carbodiimides which are not stable and converted to corresponding isoimide analogues 6 and 7 (1:6) in 96% yield. This reaction is precisely the same reaction described in parent application Ser. No. 08/613,134, except that the useful end products were inadvertently mischaracterized as the unstable carbodiimide analogs rather than isoimides. Separation of the mixture gave pure isomers 6 and 7 with long wavelength absorptions at λmax 696 and 690 nm respectively. Both isomers were characterized by proton NMR and mass spectroscopy. Refluxing the isoimide (6 and 7) with various solvents alone or with K-10 clay gave mainly the starting material 1. Treatment of isoimides (either 6 or 7) with DBU/toluene at 60° C. produced imide 8 in 60% yield. Interestingly, replacing DBU with stronger bases, such as methanolic KOH or NaOH at room temperature, gave the desired purpurin-imide in 85% overall yield (λmax 705 nm). This reaction was repeated several times using individual isoimide isomers (6 or 7), and produced the desired imide 4 in >80% yield without formation of purpurin-18 methyl ester 1. Replacing DCC with 1,1'-thiocarbonyldiimidazole under similar reaction conditions gave purpurin-imide, but in a lower yield (Table 1).

A proposed mechanism for the formation of the imide ring in accordance with the invention is shown in FIG. 2. In brief, addition of the carboxylic acid to the carbodiimide will give an O-acylisourea, an activated carboxylic acid derivative. It is now understood that these intermediate species are not stable and convert to corresponding isoimides and dicyclohexylurea. Intramolecular nucleophilic attack under basic conditions will generate cyclic imide. In tetrapyrrole chemistry, this is the first example of the formation of cyclic isoimides and imides from appropriate dicyclohexylcarbodiimide intermediate with methanolic KOH.

Related carbodiimide and isoimide analogs were prepared using bacteriopurpurin-a 12 as a substrate and converting it to the related imide derivative. Bacteriopurpurin-a 12 was isolated from R. Spheroides by following the methodology as described in U.S. patent application Ser. No. 08/247,866 by reaction of bacteriochlorin with n propanol.

Another compound 12a was obtained by treatment of bacteriochlorophyll-a from R-speroides with n-propanol. Reaction of 12a with n-hexylamine gave the amide analogs 13 and 14, which on reacting with dicyclohexylcarbodiimide is believed to produce the corresponding unstable carbodiimide derivatives 15 (minor component) and 16 (major component) which convert to corresponding isoimides with long wavelength absorption at $\lambda$max 796 nm 17 ($\epsilon$=89,000) and $\lambda$max 18 804 ($\epsilon$=109,000) respectively. Currently, the synthesis of a series of related compounds with various hydrophobic properties is in progress, e.g., (a) to increase/decrease the length of alkyl amides by opening the anhydride ring with various amines, and amino acids, (b) to replace the methylester group (at position -7, ring D) with various esters or aspartic acid analogs, (c) to replace dicyclohexylcarbodiimide with other carbodiimides, and (d) to introduce primary- or secondary alkyl ether groups at position 2- of the macrocycle.

Figure 6A:
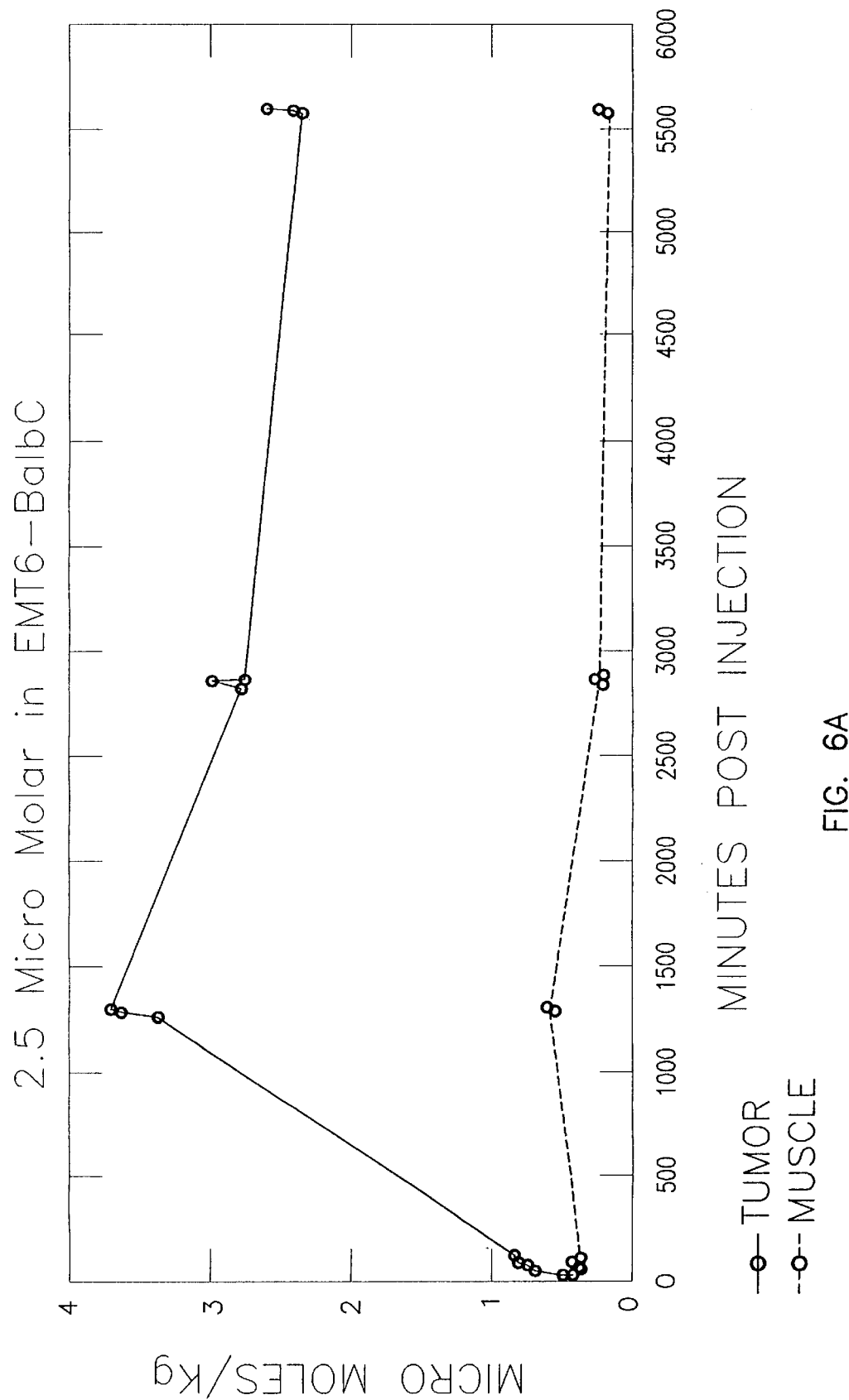
FIG. 6A is a reflection spectroscopy curve showing preferential accumulation of compound 18 in tumors over muscle.
Figure 6B:
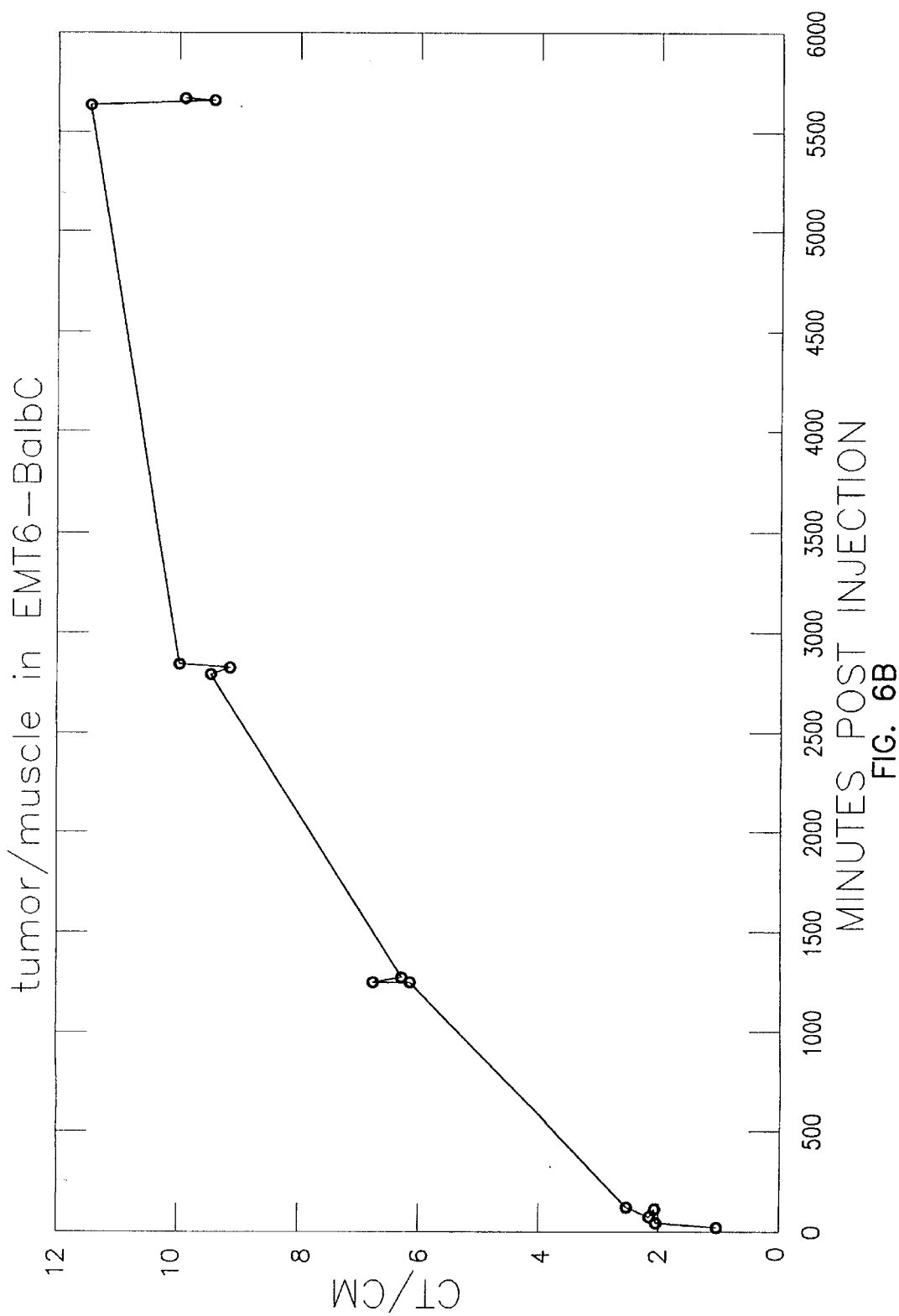
FIG. 6B is a curve showing the ratio of tumor over muscle accumulation as represented in FIG. 6A.

For a compound to be useful for PDT and IR imaging, it should have preferential accumulation in tumor. In an initial experiment, the uptake of bacteriopurpurin 18 in tumor vs. muscle was measured by in vivo reflection spectroscopy. From FIGS. 6A and 6B it can be seen that bacteriopurpurin 18 shows preferential accumulation of drug in tumor than muscles (8:1). Studies with other related compounds are currently in progress.

EXPERIMENTAL

Chemistry

Commercially available compounds and reagents were purchased from Aldrich, ACROS Organics and Sigma. Mps were taken using a Fisher-Johns hot plate melting point apparatus and are uncorrected. NMR spectra were recorded at 300 MHz on a GE instrument using $CDCl_3$ as solvent. Electronic absorption spectra were recorded using a Genesis-5 spectrophotometer.

Figure 4:
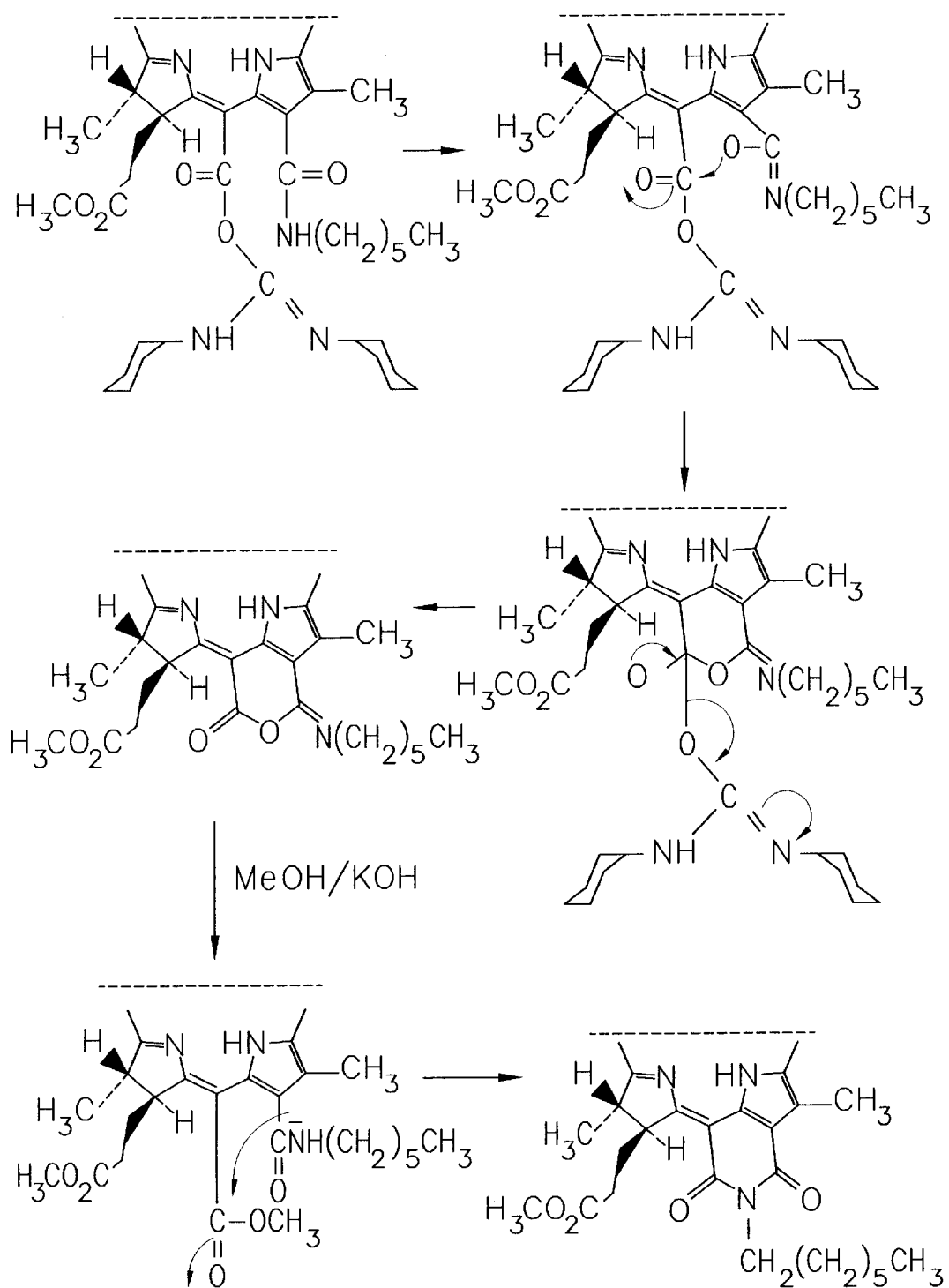
FIG. 4 is a schematic equation showing the synthetic route to cyclic isoimides and cyclic imide.
Figure 5:
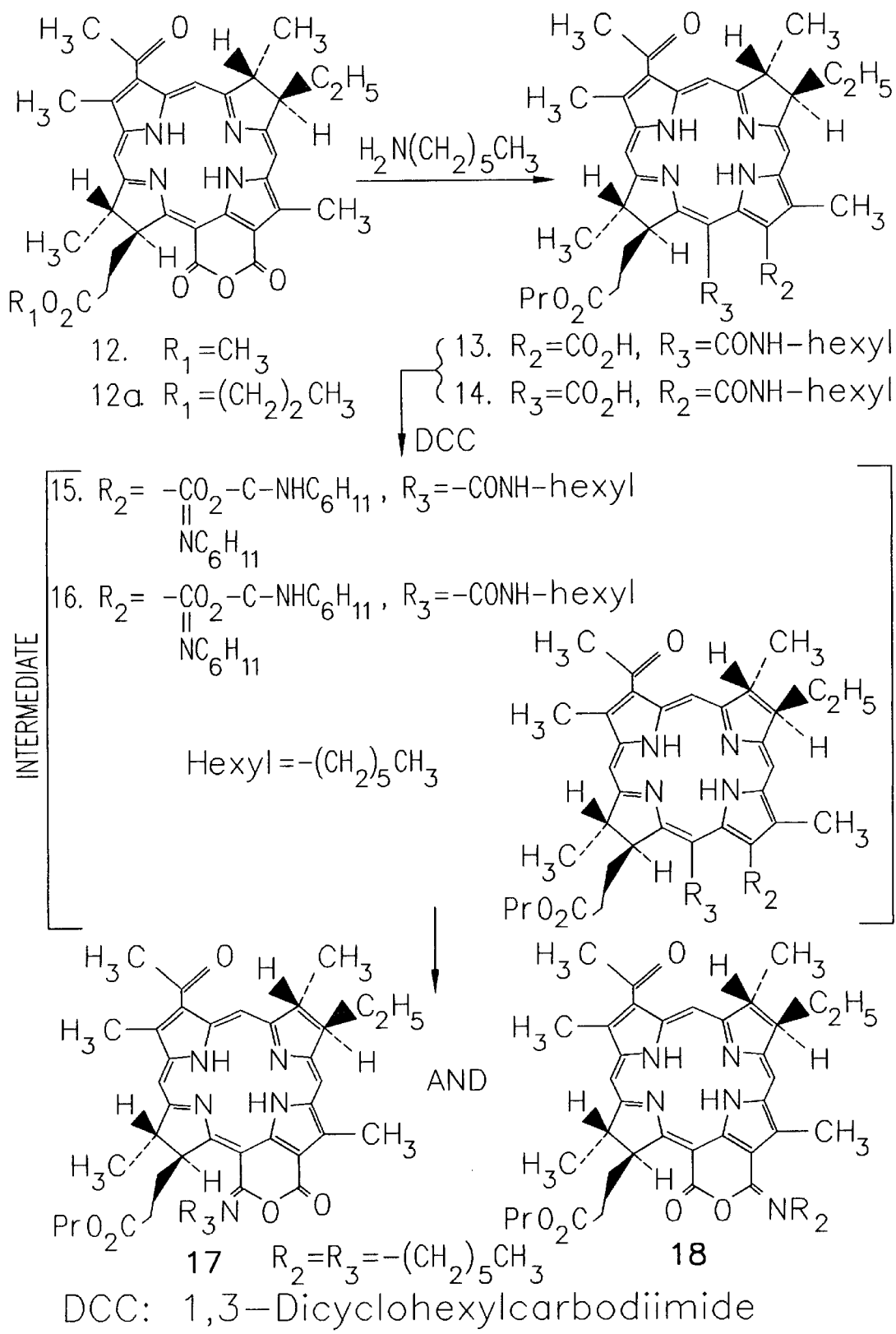
FIG. 5 is a schematic equation showing the synthetic route to isoimide bacteriochlorins 17 and 18 of the invention.

New and novel method for the preparation of purpurin-imide from isoimide via carbodiimide intermediate Purpurin-18 methyl ester 1 (200 mg, 0.34 mmol) in dichloromethane (100 ml) was treated with 1-hexylamine (2 ml, 2 mmol) and stirred at room temperature for 20 h. Spectrophotometry was used to monitor disappearance of the peak at 700 nm and appearance of a new peak at 666 nm. The solvent was then removed under high vacuum, and the residue was crystallized from dichloromethane/hexane to give hexylamine derivatives 2 (major) and 3 (minor) as a mixture in 84 and 12% yields, respectively (total: 220 mg). The reaction mixture (220 mg, 0.34 mmol) was dissolved in dichloromethane (25 ml) and reacted with dicyclohexylcarbodiimide (DCC) (400 mg, 1.75 mmol) under a nitrogen atmosphere with stirring for 12 h. The solvent was concentrated to 10 ml and left overnight in the refrigerator; dicyclohexylurea formed as a by-product was removed by filtration. The filtrate was concentrated and separated into individual isomers 4 and 5 (in the ratio of 1 to 6) using preparative plates (silica gel). The structure of these compounds were determined to be isoimide derivatives. The intermediate carbodiimides 4 and 5 were not stable. The mechanism of the formation of these compounds is shown in FIGS. 2 and 4. The yield was 90% (245 mg). For the preparation of purpurin-imide, the mixture of 6 and 7 (245 mg) was dissolved in THF (50 ml), and a methanolic solution of KOH (0.5 mg/10 ml water) was added. The reaction mixture was stirred for 5 min, and was monitored by spectrophotometry (appearance of a new peak at 705 nm). The mixture was then diluted with dichloromethane (100 ml) and washed with water (3×100 ml). The organic layer was dried over anhydrous sodium sulfate. Evaporation of the solvent gave a residue which was chromatographed on a silica gel column (elution with 2% acetone/dichloromethane). The appropriate eluates were combined. The residue obtained after evaporating the solvent was crystallized from dichloromethane/hexane, and the desired purpurin-imide 8 was obtained in 85% yield (185 mg from 1). For the syntheses of other purpurin-imides 9–11 (see Table 2), the intermediate amides, carbodiimides and isoimide analogs were not isolated, but were converted into the desired imides in one-pot without further purification.

Isoimide derivative of Bacteriopurpurin-a propyl ester (17) and (18)

Bacteriopurpurin-a propyl ester 12a (30 mg, 0.05 mmol), obtained from R. spheroides was dissolved in dichloromethane (100 ml) and was treated with 1-hexylamine (0.2 ml, 0.1 mmol). The reaction mixture was stirred at room temperature for 24 h; spectrophotometry was used to monitor the disappearance of the peak at 813 nm (due to starting material) and appearance of a new peak at 786 nm. The solvent was then removed under high vacuum, and the residue was crystallized from dichloromethane/hexane to give hexylamine derivatives 13 (minor) and 14 (major) as a mixture in 10 and 90% yields respectively. The reaction mixture (30 mg, 0.05 mmol) was dissolved in dichloromethane (25 ml) and reacted with dicyclohexylcarbodiimide (DCC) (50 mg, 0.25 mmol) under a nitrogen atmosphere with stirring for 12 h. The solvent was concentrated to 10 ml and left overnight in the refrigerator; dicyclohexylurea formed as a by-product was removed by filtration. The filtrate was concentrated and separated into individual isomers 17 and 18 (in the ratio of 1 to 9) using preparative plates (silica gel).

Yield: (28 mg, 72% overall). On the basis of NMR data, these compounds were found to be isoimide derivatives of bacteriopurpurin-a.

SPECTROSCOPIC DATA

Purpurin-18-N-hexylimide Methyl Ester (8)

[Fisher's Nomenclature]

Mp. 221°–223° C. UV/Vis: ($\lambda$ max/nm, $\epsilon$): 705 (46,000); 647 (12,000); 549 (23,000); 510 (10,000); 483 (8,000); 417 (120,000). $^1$H NMR ($\delta$ ppm, $CDCl_3$): 9.63 (s, $\beta$-meso H), 9.38 (s, $\alpha$-meso H), 8.58 (s, $\delta$-meso H), 7.92 (dd, J 19.5, 12.8 Hz, 2a-H), 6.29 (dd, J 19.5 Hz, 2b-H), 6.18 (dd, J 12.8 Hz, 2b'-H), 5.37 (d, J 8.5 Hz, 7-H), 4.48 (t, N-hexylimide-a-$CH_2$), 4.38 (q, J 8.0 Hz, 8-H), 3.84 (s, 5-Me), 3.62 (q, J 7.5 Hz, 4a-$CH_2$), 3.56 (s, OMe), 3.34 (s, 1-Me), 3.18 (3-Me), 2.65 (m, 7b-H), 2.51 (m, 7b'-H), 2.40 (m, 7a-H), 2.06 (m, 7a'-H), 2.00 (m, N-hexylimide-b,c-$CH_2CH_2$), 1.74 (d, J 8.0 Hz, 8-Me), 1.65 (t, J 7.2 Hz, 4-b Me), 1.43 (m, N-hexylimide-d,e-$CH_2CH_2$), 0.46 (t, J 7.8 Hz, N-hexylimide-f-$CH_3$), −0.08 and −0.17 (each br s, NH). m/z (LRMS): 661 (M+H).

Purpurin-18-15$^1$-hexylisoimide methyl ester (7)

Mp. 138°–139° C. $^1$H NMR ($\delta$ ppm, $CDCl_3$): 9.73 (s, $\beta$-meso H), 9.49 (s, $\alpha$-meso H), 8.65 (s, $\delta$-meso H), 7.92 (dd, J 19.4, 12.2 Hz, 2a-H), 6.31 (dd, J 19.4 Hz, 2b-H), 6.18 (dd, J 12.2 Hz, 2b'-H), 5.26 (d, J 8.5 Hz, 7-H), 4.57 (q, J 8.0 Hz, 8-H), 4.10 (m, hexyl isoimide-CH$_2$), 3.83 (s, 5-Me), 3.76 (q, J 7.5 Hz, 4a-CH$_2$), 3.58 (s, OMe), 3.46 (s, 1-Me), 3.28 (3-Me), 2.65 (m, 7b-H), 2.58-2.00 (m, 7b'-H; m, 7a-H; m, 7a'-H; m, hexyl isoimide-b,c-CH$_2$CH$_2$; 1.78 (d, J 8.0 Hz, 8-Me), 1.72 (t, J 7.2 Hz, 4-b Me), 1.61 (m, hexylamide-d, e-CH$_2$CH$_2$), 0.96 (t. J 7.8 Hz, hexyl isoimide f-CH$_3$), −0.61 and −0.88 (each br s, NH). m/z (LRMS): 661 (M+H).

Purpurin-18-13$^1$-hexyl isoimide methyl ester (6)

Mp. 142°–143° C. $^1$H NMR (δ ppm, CDCl$_3$): 9.74 (s, β-meso H), 9.57 (s, α-meso H), 8.75 (s, δ-meso H), 7.94 (dd, J 19.2, 12.5 Hz, 2a-H), 6.33 (dd, J 19.2 Hz, 2b-H), 6.15 (dd, J 12.5 Hz, 2b'-H), 5.24 (d, J 8.5 Hz, 7-H), 4.52 (q, J 8.0 Hz, 8-H), 4.06 (t, hexyl isoimide-a-CH$_2$), 3.81 (s, 5-Me), 3.74 (q, J 7.5 Hz, 4a-CH$_2$), 3.56 (s, OMe), 3.42 (s, 1-Me), 3.24 (3-Me), 2.65 (m, 7b-H), 2.51-2.00 (m, 7b'-H; m, 7a-H; m, 7a'-H; m, hexylisoimide-b,c-CH$_2$CH$_2$; m, dicyclohexylisourea-CH$_2$), 1.76 (d, J 8.0 Hz, 8-Me), 1.68 (t, J 7.2 Hz, 4-b Me), 1.58 (m, hexyl isoimide-d,e-CH$_2$CH$_2$), 0.98 (t, J 7.8 Hz, hexylisoimide-f-CH$_3$), −0.66 and −0.84 (each br s, NH). m/z (LRMS): 661 (M+H).

Purpurin-18-N-hexylimide-7-N-aspartylamide Dimethyl Ester (9)

[Fisher's Nomenclature]

Mp. 218°–219° C. UV/Vis: (λ max/nm, ε): 705 (43,200); 648 (11,000); 549 (21,000); 510 (9,200); 483 (7,800); 417 (112,000). $^1$H NMR (δ ppm, CDCl$_3$): 9.60 (s, β-meso H), 9.34 (s, α-meso H), 8.58 (s, δ-meso H), 7.90 (dd, J 19.8, 12.6 Hz, 2a-H), 6.98 (d, J 9.6, aspartate-NHCO), 6.32 (dd, J 19.8 Hz, 2b-H), 6.18 (dd, J 12.6 Hz, 2b'-H), 5.34 (d, J 8.5 Hz, 7-H), 4.46 (t, N-hexylisoimide-a-CH$_2$), 4.44 (q, J 8.0 Hz, 8-H), 4.38 (m, aspartate-CH), 3.82 (s, 5-Me), 3.69 (s, OMe), 3.64 (q, J 7.5 Hz, 4a-CH$_2$), 3.61 (s, OMe), 3.36 (s, 1-Me), 3.16 (3-Me), 2.84 (m, aspartate-CH$_2$), 2.64 (m, 7b-H), 2.51 (m, 7b'-H), 2.46 (m, 7a-H), 2.06 (m, 7a'-H), 1.99 (m, N-hexylimide-b,c-CH$_2$CH$_2$), 1.75 (d, J 8.0 Hz, 8-Me), 1.66 (t, J 7.5 Hz, 4-b Me), 1.45 (m, N-hexylimide-d,e-CH$_2$CH$_2$), 0.96 (t, J 7.8 Hz, N-hexylimide-f-CH$_3$), −0.38 and −0.11 (each br s, NH). m/z (LRMS): 791 (M+H).

Purpurin-18-N-hexylimide-7-N-Aspartylamide-di-tert-butyl Ester (10)

Mp. 190°–192° C. UV/Vis: (λ max/nm, ε): 705 (42,800); 648 (11,000); 549 (20,000); 510 (9,000); 483 (7,500); 417 (110,000). $^1$H NMR (δ ppm, CDCl$_3$): 9.63 (s, β-meso H), 9.37 (s, α-meso H), 8.58 (s, δ-meso H), 7.86 (dd, J 19.4, 12.5 Hz, 2a-H), 6.74 (d, J 9.6 Hz, aspartate-NHCO), 6.32 (dd, J 19.4 Hz, 2b-H), 6.21 (dd, J 12.5 Hz, 2b'-H), 5.33 (d, J 8.5 Hz, 7-H), 4.66 (q, J 8.0 Hz, 8-H), 4.41 (t,N-hexylimide-CH$_2$), 3.99 (m, aspartate-CH), 3.84 (s, 5-Me), 3.68 (q, J 7.5 Hz, 4a-CH$_2$), 3.36 (s, 1-Me), 3.18 (3-Me), 2.76 (m, aspartate-CH$_2$), 2.65 (m, 7b-H), 2.51 (m, 7b'-H), 2.46 (m, 7a-H), 2.06 (m, 7a'H), 1.92 (m, N-hexylimide-b,c-CH$_2$CH$_2$), 1.68 (d, J 8.0 Hz, 8-Me), 1.66 (t, J 7.5 Hz, 4-b Me), 1.37 (s, aspartate-$^t$Bu), 1.34 (s, aspartate-$^t$Bu), 1.14 (m, N-hexylimide-d,e-CH$_2$CH$_2$), 0.95 (t, J 7.8 Hz, N-hexylimide-f-CH$_3$), −0.38 and −0.11 (each br s, NH). Mass: m/z (HRMS): requires for C$_{51}$H$_{67}$N$_6$O$_7$: 875.5071. Found 875.5016.

Purpurin-18-N-glycylimide-tert-Butyl Ester-7-aspartylamide-di-tert-butyl Ester (11)

[Fisher's Nomenclature]

Mp. 138°–139° C. UV/Vis: (λ max/nm, ε): 705 (41,300); 649 (10,000); 549 (19,000); 510 (8,700); 483 (7,300); 417 (105,000). $^1$H NMR (δ ppm, CDCl$_3$): 9.61 (s, β-meso H), 9.35 (s, α-meso H), 8.56 (s, δ-meso H), 7.88 (dd, J 19.5, 12.6 Hz, 2a-H), 6.65 (d, J 9.5 Hz, aspartate-NHCO), 6.26 (dd, J 19.5 Hz, 2b-H), 6.16 (dd, J 12.5 Hz, 2b'-H), 5.27 (d, J 8.5 Hz, 7-H), 5.18 (q, glycine-CH$_2$), 4.68 (q, J 7.5 Hz, 8-H), 4.38 (m, aspartate-CH), 3.38 (s, 5-Me), 3.64 (q, J 7.5 Hz, 4a-CH$_2$), 3.35 (s, 1-Me), 3.16 (3-Me), 2.79 (m, aspartate-CH$_2$), 2.66 (m, 7b-H), 2.54 (m, 7b'-H), 2.46 (m, 7a-H), 2.01 (m, 7a'-H), 1.73 (d, J 7.5 Hz, 8-Me), 1.67 (t, J 7.5 Hz, 4-b Me), 1.58 (s, glycine-$^t$Bu), 1.38 (s, aspartate-$^t$Bu), 1.34 (s, aspartate-$^t$Bu), 0.10 and −0.04 (each br s, NH). m/z (LRMS) 905.4 (M+H).

Bacteriopurpurin-a 17-propyl Ester (12a)

[Fisher's Nomenclature]

UV/Vis (CH$_2$Cl$_2$, λmax, nm): 813 (56,000); 543 (32,000); 408 (48,000); 363 (102,000). NMR (CDCl$_3$, δ ppm): 9.21 (s, 1H, 5-H), 8.79 (s, 1H, 10-H), 8.62 (s, 1 H, 20-H), 5.14 (d, 1H, J=8.0, 17-H), 4.30 (m, 2H, 3-H, 18-H), 4.08 (m, 1H, 8-H), 3.94 (t, 2H, CO$_2$CH$_2$), 3.66 (s, 3H, 12-Me), 3.55 (s, 3H, 2-Me), 3.17 (s, 3H, 3-Me), 2.73 (m, H, 17b-H), 2.41 (m, 5H, CH$_2$CH$_2$CH$_3$+8a-CH$_2$+7b'-H), 2.14 (m, H, 17a-H), 1.98 (m, H, 17a'-H), 1.81, 1.73 (each d, 3H, J=8.0, 18-Me, 7-Me), 1.11 (t, 3H, J=7.8, 3-b Me), 0.83 (t, 3H, J=8.2, CH$_2$CH$_2$CH$_3$), −0.30 and −0.67 (each br s, 2H, 21, 23-NH).

Bacteriopurpurin-a-15$^1$-N-hexylisoimide (17)

[Fisher's Nomenclature]

Uv/Vis: λmax: 795 (67,000); 537 (24,500); 410 (50,400); 363 (89,600). NMR (CDCl$_3$, δ ppm): 9.21 (s, 1H, 5-H), 8.77 (s, 1H, 10-H), 8.68 (s, 1H, 20-H), 5.35 (m, 2H, NHCO+17-H), 4.32 (m, 2H, 3-H, 18-H), 4.11 (m, 3H, 8-H+hexylamide-a-CH$_2$), 3.91 (t, 2H, CO$_2$CH$_2$), 3.69 (s, 3H, 12-Me), 3.58 (s, 3H, 2-Me), 3.19 (s, 3H, 3-Me), 2.62 (m, H, 17b-H), 2.44 (m, 5H, CH$_2$CH$_2$CH$_3$+8a-CH$_2$+7b'-H), 2.14 (m, 6H, 17a-H+hexylisoimide-b,c-CH$_2$+17a'-H), 1.93, 1.84 (each d, 3H, J=8.0, 18-Me, 7-Me), 1.60 (m, 4H, hexylamide-d,e-CH$_2$, 1.11 (t, 3H, J=7.8, 3-b Me), 0.97 (t, 3H, hexylamide-f-CH$_3$), 0.88 (t, 3H, J=8.2, CH$_2$CH$_2$CH$_3$), −0.68 and −1.03 (each br s, 2H, 21, 23-NH). Mass: LRMS:708(M+H)

Bacteriopurpurin-a-13$^1$-N-hexyl isoimide (18)

[Fisher's Nomenclature]

UV/Vis (λ max/nm, ε): 804 (82,800); 539 (33,200); 409 (59,400); 360 (94,000). NMR (CDCl$_3$, δ ppm): d H: 9.38 (s, 1H, 5-H), 8.88 (s, 1H, 10-H), 8.73 (s, 1H, 20-H), 5.46 (m, 1H, NHCO), 5.18 (d, 1H, J=8.0, 17-H), 4.34 (m, 2H, 3-H, 18-H), 4.17 (m, 1H, 8-H), 3.91 (m, 2H, hexylisoimide-a-CH$_2$), 4.06 (t, 2H, CO$_2$CH$_2$), 3.68 (s, 3H, 12-Me), 3.59 (s, 3H, 2-Me), 3.19 (s, 3H, 3-Me), 2.73 (m, H, 17b-H), 2.42 (m, 5H, CH$_2$CH$_2$CH$_3$+8a-CH$_2$+7b'-H), 2.14 (m, H, 17a-H), 2.08 (m, 5H, hexylamide-b,c-CH$_2$+17a'-H), 2.01, 1.93 (each d, 3H, J=8.0, 18-Me, 7-Me), 1.57 (m, 4H, hexylisoimide-d,e-CH$_2$), 1.12 (t, 3H, J=7.8, 3-b Me), 0.96 (t, 3H, hexylamide-f-CH$_3$), 0.87 (t, 3H, J=8.2, CH$_2$CH$_2$CH$_3$), −0.86 and −1.13 (each br s, 2H, 21, 23-NH). Mass: LRMS:708(M+1)

BIOLOGICAL STUDIES

Determination of Drug Uptake

The absorption spectrum of a compound in living tissue can be recorded using an instrument and technique which we have developed. The experiment measures the light which scatters through the tissue. The light originates in a high pressure Xenon arc lamp and passes through a grating monochromator to a 90 Hz chopper and then into a 400 $\mu$m diameter quartz fiber. The distal end of this fiber is placed in contact with the tissue (e.g., an experimental mouse tumor) and the light is collected by a second fiber placed in contact with the tissue at a fixed distance (3 to 5 mm) from the first fiber. The noninvasive character of this measurement makes data collection possible at a number of time points after the i.v. injection of an experimental light absorbing compound (e.g., a potential photosensitizer). The light signal is detected by a photodiode. The photo current is converted into a voltage, amplified by a tuned (90 Hz) amplifier and synchronously detected. The chopping at 90 Hz and synchronous detection makes examining spectra under normal room lighting possible.

For these experiments, the mice were first anesthetized using either Pentobarbital or Ketamine Xylazine i.p. The optical power as a function of wavelength was recorded before the i.v. injection of the sensitizer. The monochromator is set to the expected longest wavelength of the experimental drug's in vitro absorption spectrum. The drug may then administered by tail vein injection and the light signal recorded. The second spectrum contains a component caused by the presence of the drug in the tumor. This in vivo drug absorption spectrum is best displayed by taking the ratio of the post-injection spectrum to the pre-injection spectrum. This ratio offers the same advantages as a double beam absorption spectrophotometer. The pre-injection mouse data can be thought of as the reference beam sample (typically a cuvette and solvents) and the post-injection data as the sample beam containing everything in the reference beam plus the experimental drug. The ratio of these two spectra is certainly not influenced by the wavelength dependence of the light signal which characterizes the instrument. As a safeguard against day to day or hour to hour drift in the total light output of the lamp, both spectra (pre- and post-injection) are normalized by dividing the signal strength at a wavelength where the drug absorption is negligible.

Photosensitizing Efficacy

Part I—In vivo Efficacy of Bacteriochlorins 17 and 18 using SMT-F Tumor Model

The new photosensitizer was screened in a mouse/tumor model system. A model system consisted of observing the size reduction of the SMT-F tumor, a fast growing spontaneous mouse mammary tumor subline, transplanted subcutaneously to male or female DBA/2 HA-DD mice. The tumor line was maintained in vivo via serial transplantation in the same mouse strain. DBA/2 Ha-DD mice are readily available and were obtained locally.

When mice were both the appropriate age (approximately 6 weeks) and weight (approximately 20 g), small pieces of tumor (1–2 mm cube) were transplanted with a 18 gauge trocar from a donor tumor to recipient mouse. This technique provides for relatively uniform tumor size and allows location of the tumor in the right auxiliary region of the animal within each experimental group. Only animals with single tumors were chosen for experiments. When tumor reached 4–5 mm in diameter, the animals were injected with the potential photosensitizer chosen from the group described above. Prior to irradiation, the fur overgrown and surrounding the tumor was removed with electric clippers. Three or twenty four hours after injecting the drug, the mouse was placed in a custom-made aluminum holder.

Irradiation Conditions

Standard light dose was 75 mW/cm$^2$ for 30 min for a total incident dose of 135 J/cm$^2$ from a tunable dye laser tuned to the maximum red absorption peak. Spectra Physics 2040, a quartz fiber fitted with a microlens was interfaced to the dye laser deliver a uniform field of light. Laser output was measured with a power meter. Further studies at various light doses and treatment conditions are currently in progress.

Experimental Procedure

Following light exposure, the mice were kept in groups of 5 per cage and supplied with pelleted food and tap water ad libitum. Tumor size and gross appearance of both tumor and overlying surrounding skin was monitored daily for 80 days after photoillumination unless growth of non-responsive tumor require early sacrifice of those animals.

The photosensitizer was dissolved in known quantity of Tween 80 (Aldrich) surfactant and diluted by a factor of 10 with saline solution to produce a final Tween 80 concentration of 10–20%. The solution was then filtered through a syringe filter. The concentration of the solution was determined on the basis of the extinction coefficient value of the photosensitizer at the longest wavelength absorption. Absorption spectra were obtained using a Spectronic Genesis5 spectrophotometer.

Before injecting the drug into mice, the purity of the compounds was ascertained by analytical HPLC using Spectra Physics HPLC, connected with C8 reverse phase column, eluted with methanol/water by adjusting the pH to 7.0 using phosphate buffer.

Alkylimide Derivatives of Bacteriochlorins

Procedures similar to preparation of N-hexylimide derivatives were followed except that various other alkyl amines were substituted for hexylamine.

The resulting compounds were tested for in vivo antitumor activity.

4–6 mm diameter tumors (DBA/2 mice transplanted with SMT-F tumors) were exposed to 75 mW/cm$^2$ for 30 minutes to deliver light (135 J/cm$^2$) from a tunable dye laser tuned to a maximum red absorption peak. The tumors were non-palpable and five mice were used per group.

The results are in Table 4. The results indicate a large suppressive effect for isomers where the extended alkyl group is closest to the amino acid group.

Part II—In vivo efficacy of bacteriochlorins 17 and 18 using Radiation Induced Fibrosarcoma (RIP) Tumor Model A mixture of bacteriochlorins 17 and 18 was also evaluated for in vivo PDT efficacy using another model (RIF tumor model routinely used in our laboratory. In brief, six mice per group with appropriate tumor size (4–5 mm) were chosen for the experiment. As shown in Table 3, the animals were treated at variable doses of light and drug. Beginning 24 h after PDT, and at least every other day thereafter, tumors were measured in orthogonal diameters with an electronic caliper (ultra-Cal Mark III; Fred V. Fowler Co., Boston Mass.). Each measurement was automatically recorded, where the tumor volume, V, was calculated using the formula $v=(lw^2)/2$, where l is the longest axis of the tumor and w is the axis perpendicular to l. The time for growth to the tumor to 400 mm$^3$ was then estimated by interpolation of the times just before and after 400 mm$^3$ was reached. Tumor response was recorded on the basis of the number of animals which were found to be tumor free. Appropriate controls were carried out with tumor-bearing mice which received no treatment at all, or received light or photosensitizer only.

TABLE 1

Formation of purpurin-18 with cyclic anhydride and imide rings at various reaction conditions

| Method No. | Conditions | Yield (%) | | |
|---|---|---|---|---|
| | | imide 4 | anhydride 1 | starting materials (5 & 6) |
| 1. | THF, refluxing for 4 h. | 5 | 70 | 25 |
| 2. | Imidazole, 140° C., 1 h | Decomposition products | | |
| 3. | K-10 Clay, CH$_2$Cl$_2$, 24 h | 10–12 | 80–85 | 0 |
| 4. | CH$_2$Cl$_2$, 10 days | 15–20 | 20–25 | 50 |
| 5. | DCC with: | | | |
| | a. K-10 Clay, RT | 0 | 0 | 100 |
| | b. DBU, RT | 0 | 0 | 100 |
| | c. DBU, toluene, reflux 2 h | 60 | 0 | 40 |
| | d. KOH/MeOH RT, 10 min | 85 | 0 | 0 |
| 6. | TCD with: | | | |
| | a. DBU, RT | 0 | 0 | 100 |
| | b. DBU, toluene, reflux 2 h | 10 | 50 | — |
| | c. DBU, THF 60° C. | 30 | 0 | 60 |
| | d. KOH/MeOH RT, 10 min | 10 | 0 | 90 |

DCC: Dicyclohexylcarbodiimide; DBU, 1,8-Diazabicyclo(5,4,0)undec-7-ene; RT, Room temperature; TCD, 1,1-Thiocarbonyldiimidazole.

TABLE 2

Yields of purpurin-imides

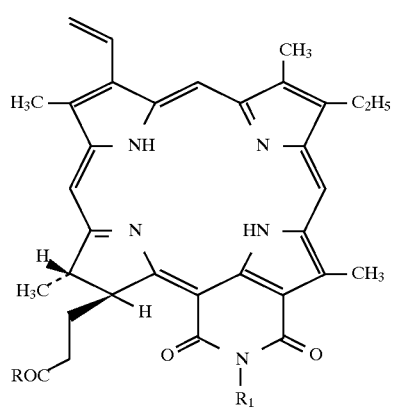

| Compound No. | R | R$_1$ | % yield |
|---|---|---|---|
| 8 | OMe | n-hexyl | 85 |
| 9 | Asp-di-methyl ester | n-hexyl | 89 |
| 10 | Asp-di-tert- butyl ester | n-hexyl | 87 |
| 11 | Asp-di-tert- butyl ester | tert-butyl Gly | 78 |

TABLE 3

PDT Efficacy in Mice Transplanted with Radiation Induced Fibrosarcoma (RIF) Tumor with a Mixture of Bacteriochlorins 17 and 18

| Drug Dose | Light Dose | Timer after | Tumor Response days | | |
|---|---|---|---|---|---|
| µmol/kg | Rate mW/cm$^2$ | Injection hrs | 1–2 | 7 | 14 |
| 0.20 | 75 | 24 | 100% | 100% | 80% |
| 0.20 | 30 | 24 | 80% | 60% | 40% |
| 0.25 | 75 | 24 | 100% | 100% | 80% |
| 0.25 | 30 | 24 | 80% | 80% | 60% |

TABLE 4

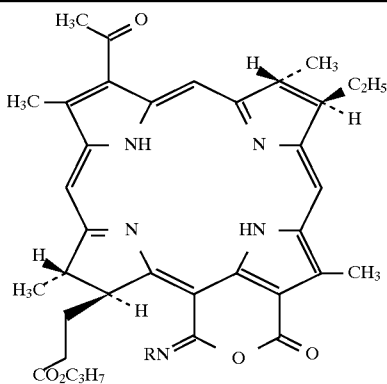

MINOR (795 NM)
17. R = (CH$_2$)$_5$CH$_3$
19. R = (CH$_2$)$_6$CH$_3$
21. R = (CH$_2$)$_2$CH$_3$
23. R = (CH$_2$)$_9$CH$_3$

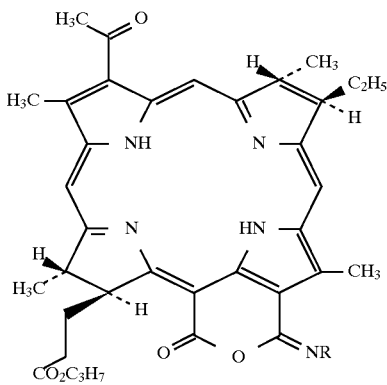

(MAJOR (804 NM))
18. R = (CH$_2$)$_5$CH$_3$
20. R = (CH$_2$)$_6$CH$_3$
22. R = (CH$_2$)$_2$CH$_3$
24. R = (CH$_2$)$_9$CH$_3$

Comparative in vivo Antitumor Activity of Bacteriochlorins

| Compound | Dose ($\mu$mol/kg) | in vivo absorption ($\lambda$ max) | Time (h) betw. injection and light treatment | Tumor response (d)[†],* | | |
|---|---|---|---|---|---|---|
| | | | | 1–2 | 15 | 30+ |
| Mixture of 17 and 18 | 0.47 | 804 | 24 | REGROWTH ON DAY 15 | | |
| 20 | 0.47 | 804 | 24 | NO RESPONSE | | |
| 22 | 0.47 | 804 | 24 | REGROWTH ON DAY 4 | | |
| Mixture of 23 and 24 | 0.47 | 804 | 24 | 100 | 40 | 20 |

[†]4–5 mm diameter tumors were exposed to 75 MW/cm$^2$ for 30 min to deliver 135 J/cm$^2$ light from a tunable dye laser tuned to the maximum red absorption peak.
d = days.
*Non-palpable tumors.

What is claimed is:

1. A compound of the formula:

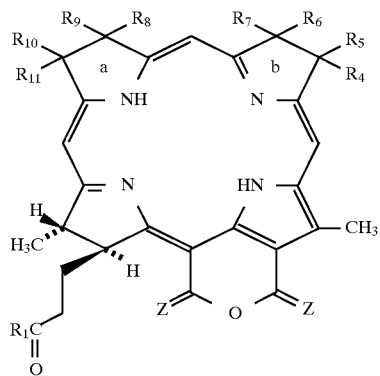

where z is =O or =NR$_{14}$; R$_1$ is an amino acid group, a polyamine group, a polyether group or OR$_{13}$ where R$_{13}$ is alkyl; R$_{14}$ is alkyl, substituted alkyl, a polyamine group, or an amino acid group; R$_4$ through R$_{11}$ are —H, —OH, alkyl, alkoxy, alkenyl, alkylene, aryl, or aryloxy or a carbonyl containing group, wherein carbon containing groups may be substituted with carbonyl, hydroxy, phosphoro, carboxy, halo, sulfo, amino and ether substituents, provided that; R$_4$ may be taken together with R$_5$ to form =O; R$_6$ may be taken together with R$_7$ to form =O; R$_8$ may be taken together with R$_9$ to form =O; R$_{10}$ may be taken together with R$_{11}$ to form =O; and R$_4$ and R$_7$ may together form a chemical bond and R$_8$ and R$_{11}$ may together form a chemical bond; and R$_{12}$ is hydrogen or lower alkyl; provided that if one z is =O, the other z is =NR$_{14}$.

2. The compound of claim 1 wherein R$_{11}$ and R$_{12}$ are —CH$_3$.

3. The compound of claim 1 wherein R$_9$ is —COCH$_3$.

4. The compound of claim 1 having the formula:

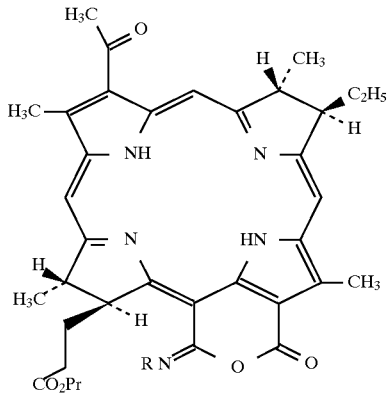

where R is normal alkyl of 2 through 12 carbon atoms.

5. The compound of claim 1 having the formula:

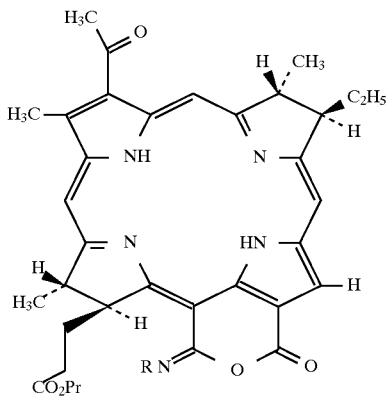

where R is normal alkyl of 2 through 12 carbon atoms.

6. The compound of claim 2 wherein R$_9$ is —COCH$_3$.

7. A method for the preparation of an isoimide derivative of purpurin comprising reacting a purpurin with 1-hexylamine to open the anhydride ring followed by reaction with a carbodiimide to obtain the isoimide derivative of purpurin, said purpurin being reacted with 1-hexylamine, said purpurin having the formula:

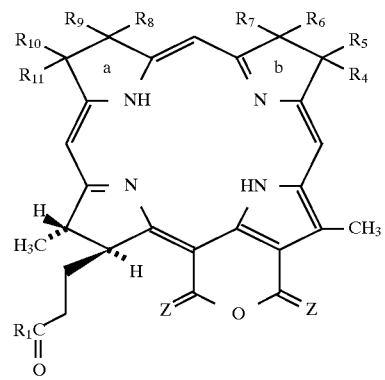

wherein z is =O or NR$_{14}$; R$_1$ is an amino acid group, a polyamine group, a polyether group or OR$_{13}$ where R$_{13}$ is alkyl; R$_{14}$ is alkyl, or substituted alkyl, a polyamine group, or an amino acid group; R$_4$ through R$_{11}$ are —H, —OH, alkyl, alkoxy, alkenyl, alkylene, aryl, or aryloxy or a carbonyl containing group, wherein carbon containing groups may be substituted with carbonyl, hydroxy, phosphoro, carboxy, halo, sulfo, amino and ether substituents provided that; R$_4$ may be taken together with R$_5$ to form =O; R$_6$ may be taken together with R$_7$ to form =O; R$_8$ may be taken together with R$_9$ to form =O; R$_{10}$ may be taken together with R$_{11}$ to form =O; and R$_4$ and R$_7$ may together form a chemical bond and R$_8$ and R$_{11}$ may together form a chemical bond; and R$_{12}$ is hydrogen or lower alkyl; provided that if one z is =O, the other z is —NR$_{14}$.

8. A method for the manufacture of purpurin imide comprising reacting the compound of claim 1 with alkali metal hydroxide.

9. A method for the manufacture of purpurin imide comprising reacting the compound of claim 2 with an alkali metal hydroxide.

10. A method for the manufacture of purpurin imide comprising reacting the compound of claim 6 with an alkali metal hydroxide.

11. A method for the manufacture of purpurin imide comprising reacting the compound of claim 8 with an alkali metal hydroxide.

12. A method for the manufacture of purpurin imide comprising reacting the compound of claim 9 with an alkali metal hydroxide.

13. A method for the manufacture of purpurin imide comprising reacting the compound of claim 10 with an alkali metal hydroxide.

14. A method for the manufacture of purpurin imide comprising reacting the purpurin derivative from claim 7 with alkali metal hydroxide.

15. A method for the manufacture of purpurin imide comprising reacting the purpurin derivative from claim 7 with alkali metal hydroxide.

16. A method for the manufacture of an imide derivative of purpurin comprising:

reacting hexylamine with a chlorin or bacteriochlorin having a macrocycle with a six membered anhydrid ring fused thereto, said macrocycle containing a and b rings which may be saturated or unsaturated at $R_4$ to $R_{11}$ positions and which $R_4$ to $R_{11}$ positions may contain at least one group selected from the group consisting of hydrogen, hydroxy, formal, substituted and unsubstituted alkyl, alkoxy, alkenyl, aryl and aryloxy, wherein carbon containing groups may be substituted with a substituent selected from carbonyl, hydroxy, phosphoro, carboxy, halo, sulfo, amino and ether, to obtain a purpurin derivative; and reacting the obtained purpurin derivative with a carbodiimide to obtain the imide derivative of purpurin.

* * * * *